(12) United States Patent
Solomon

(10) Patent No.: US 8,980,547 B2
(45) Date of Patent: Mar. 17, 2015

(54) METHOD FOR TREATING NEURODEGENERATIVE TAUOPATHY

(75) Inventor: Beka Solomon, Herzliya Pituach Herzliya (IL)

(73) Assignee: Ramot at Tel Aviv University Ltd., Tel Aviv (IL)

( * ) Notice: Subject to any disclaimer, the term of this patent is extended or adjusted under 35 U.S.C. 154(b) by 0 days.

(21) Appl. No.: 14/004,615

(22) PCT Filed: Mar. 12, 2012

(86) PCT No.: PCT/US2012/028762
§ 371 (c)(1),
(2), (4) Date: Nov. 25, 2013

(87) PCT Pub. No.: WO2012/125555
PCT Pub. Date: Sep. 20, 2012

(65) Prior Publication Data
US 2014/0086880 A1    Mar. 27, 2014

Related U.S. Application Data

(60) Provisional application No. 61/451,948, filed on Mar. 11, 2011, provisional application No. 61/492,059, filed on Jun. 1, 2011, provisional application No. 61/583,816, filed on Jan. 6, 2012.

(51) Int. Cl.
*C12Q 1/70* (2006.01)

(52) U.S. Cl.
USPC .................................... 435/5; 434/93.6

(58) Field of Classification Search
USPC .......................... 435/7.1, 5; 424/93.6; 800/12
IPC ........................ A61K 35/76; C12N 2795/1413
See application file for complete search history.

(56) References Cited

U.S. PATENT DOCUMENTS

| | | | |
|---|---|---|---|
| 7,867,487 B2 * | 1/2011 | Solomon et al. | 424/93.6 |
| 2003/0148404 A1 * | 8/2003 | Michaelson | 435/7.21 |
| 2009/0324554 A1 * | 12/2009 | Solomon et al. | 424/93.6 |
| 2011/0182948 A1 * | 7/2011 | Solomon et al. | 424/400 |

FOREIGN PATENT DOCUMENTS

| | | |
|---|---|---|
| WO | 2006/083795 A1 | 8/2006 |
| WO | 2008/011503 A2 | 1/2008 |
| WO | 2010/060073 A2 | 5/2010 |

OTHER PUBLICATIONS

Ling T. et al. Purification of Filamentous Bacteriophage M13 by Expanded Bed Anion Exchange Chromatograpy. J of Microbiology 42(3)228-232, Sep. 2004.*
Solomon et al., "S4-04-02: Phage Therapy of Alzheimer's Disease," Alzheimer's & Dementia: The Journal of the Alzheimer's Association, Elsevier, New York, NY, US, vol. 4, No. 4, Jul. 1, 2008, pp. 1552-5260. (Abstract).
Dimant et al., "Modulation Effect of Filamentous Phage on alpha-synuclein Aggregation," Biochemical and Biophysical Research Communications, Academic Press Inc., Orlando, FL, U.S. vol. 383, No. 4, Jun. 12, 2009, pp. 491-496.
Marvin et al., Filamentous Bacterial Viruses, Bacteriological Reviews, 33(2):172-209 (1969).
Rasched et al., Ff Coliphages: Structural and Functional Relationships, Microbiological Reviews, 50(4):401-427 (1986).
Chiti et al., Protein misfolding, functional amyloid, and human disease, Annu. Rev. Biochem., 75:333-66 (2006).

* cited by examiner

*Primary Examiner* — Ralph Gitomer
(74) *Attorney, Agent, or Firm* — Browdy and Neimark, PLLC

(57) ABSTRACT

The present invention is directed to a filamentous bacteriophage for use in treating a neurodegenerative tauopathy or susceptibility to a neurodegenerative tauopathy and a method of using the bacteriophage for reducing the formation of fibrils of tau protein or for disaggregating pre-formed fibrils of tau protein, such as in a patient suffering from neurodegenerative tauopathy. The filamentous bacteriophage used in the present invention does not display (i) a mammalian cell internalization signal (ii) a β-amyloid antigen or an antibody to β-amyloid, or (iii) a tau protein antigen or an antibody to tau protein.

14 Claims, 5 Drawing Sheets

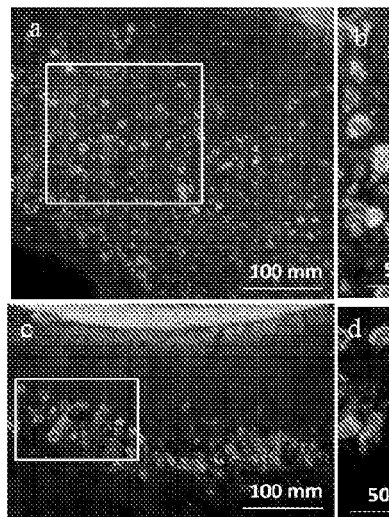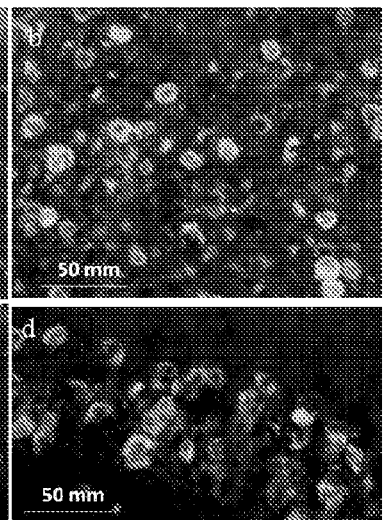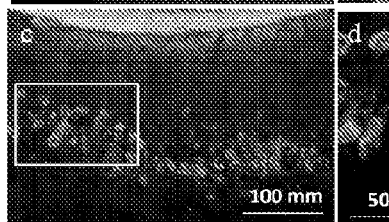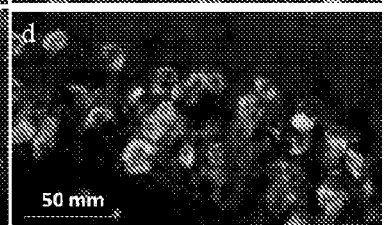
Figure 3A  Figure 3B  Figure 3C  Figure 3D
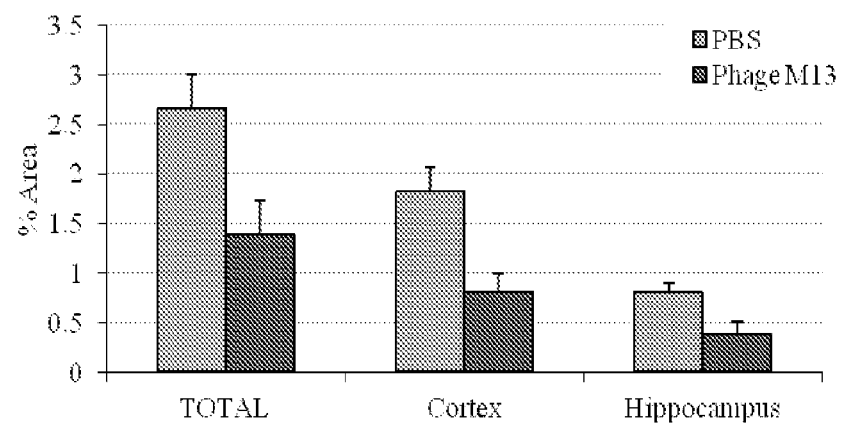
Figure 3E

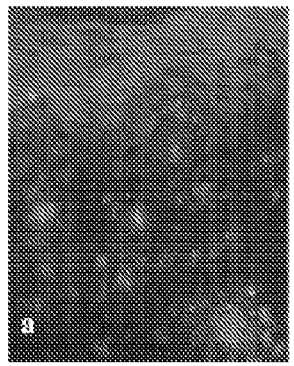 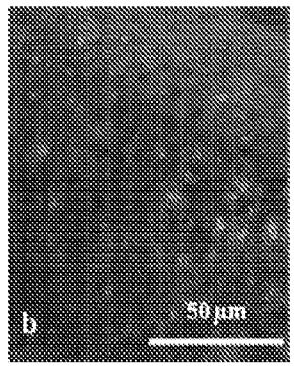 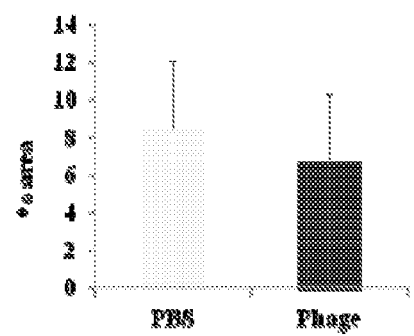
Figure 4A    Figure 4B    Figure 4C
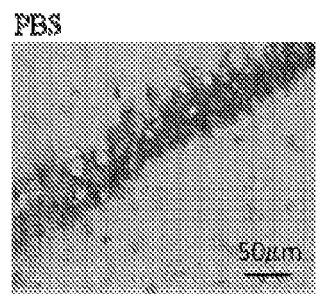 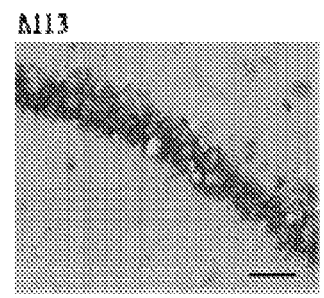
Figure 5A    Figure 5B
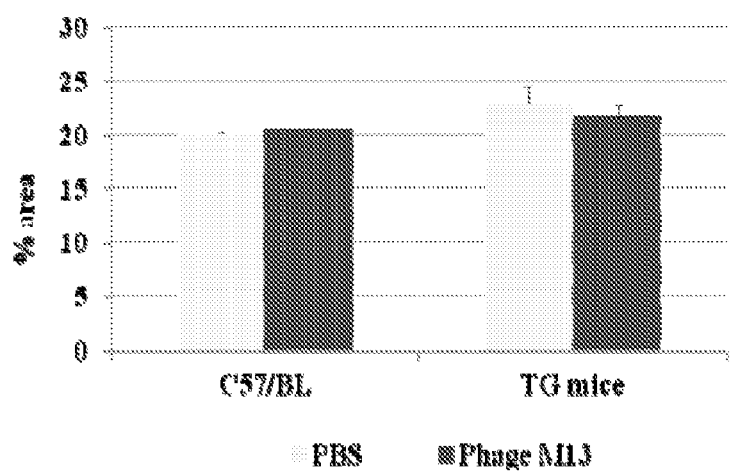
Figure 5C

SEQUENCE LISTING

```
<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Asp Gly Glu Ala
1

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Ile Arg Val Val Met
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic

<400> SEQUENCE: 3

Pro His Ser Arg Asn
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Arg Phe Tyr Val Val Met Trp Lys
1               5
```

METHOD FOR TREATING NEURODEGENERATIVE TAUOPATHY

BACKGROUND OF THE INVENTION

1. Field of the Invention

The present invention relates to the field of therapeutics and compositions for use in the treatment of neurodegenerative tauopathies.

2. Description of the Related Art

Tauopathies are a group of neurodegenerative diseases with the pathological hallmark of abnormal intracellular aggregates of the microtubule-associated tau protein in the form of fibrils/filaments/fibers in the brain. These tauopathies include diseases such as Alzheimer's disease, Amyotrophic lateral sclerosis/parkinsonism-dementia complex, Argyrophilic grain dementia, Corticobasal degeneration, Creutzfeldt-Jakob disease, Dementia pugilistica, Diffuse neurofibrillary tangles with calcification, Down's syndrome, Frontotemporal dementia with parkinsonism linked to chromosome 17, Gerstmann-Straussler-Scheinker disease, Hallervorden-Spatz disease, Myotonic dystrophy, Niemann-Pick disease type C, Non-Guamanian motor neuron disease with neurofibrillary tangles, Pick's disease, Postencephalitic parkinsonism, Prion protein cerebral amyloid angiopathy, Progressive subcortical gliosis, Progressive supranuclear palsy, Subacute sclerosing panencephalitis, Tangle only dementia (Lee et al., 2001). While tauopathies have diverse phenotypes and clinical characteristics, they all share in common the presence of neurofibrillary tangles (NFT) of insoluble, hyperphosphosylated tau in the form of fibrils/filaments/fibers, e.g., twisted, straight or paired helical.

Tau protein is a microtubule-associated protein encoded by the MAPT gene located in chromosome 17, and it exists in neurons as a soluble phosphosylated protein involved with stabilizing and promoting the polymerization of microtubules. Abnormal hyperphosphosylation of tau, as seen in neurofibrillary tangles, decreases tau protein's microtubule binding ability and inhibits its ability to promote microtubule assembly.

Therapeutic strategies directed to tauopathies, as reviewed in Pritchard et al. (2011), include (i) small molecule inhibitors of tau aggregation such as the phenothiazine compound methylene blue and the N3 benzothiazole derivative, (ii) microtubule stabilizing agents such as taxol (paclitaxel), (iii) tau immunotherapy, (iv) autophagy activators, such as rapamycin, to effect clearance of insoluble and pathological tau fibrils, and (v) antioxidant molecules, such as vitamins C and E, glutathione, ubiquinone, and a ubiquinone derivative MitoQ.

Filamentous bacteriophages are a group of structurally related viruses which contain a circular single-stranded DNA genome. Filamentous bacteriophages are neither lytic nor lysogenic and they do not kill their host during productive infection. The phages that infect *Escherichia coli* containing an F factor are collectively referred to as Ff bacteriophages. These bacteriophage do not infect eukaryotice cells, including mammalian cells.

The filamentous bacteriophages are flexible rods about 1 to 2 microns long (for Ff bacteriophage, only about 1 micron in length) and 6 nm in diameter, with a helical shell of protein subunits surrounding a single stranded, circular DNA genomic core. For filamentous bacteriophage in the Ff family (those filamentous bacteriophage, M13, fd, and f1, that infect *E. coli* through the F-pilus), the two main coat proteins, protein pIII and the major coat protein pVIII, differ in the number of copies of the displayed protein. While pIII is presented in 3-5 copies, pVIII is found in ~3000 copies. The approximately 50-residue major coat protein pVIII subunit is largely α-helical and the axis of the α-helix makes a small angle with the axis of the virion. The protein shell can be considered in three sections: the outer surface, occupied by the N-terminal region of the subunit, rich in acidic residues that interact with the surrounding solvent and give the virion a low isoelectric point; the interior of the shell, including a 19-residue stretch of apolar side-chains, where protein subunits interact mainly with each other; and the inner surface, occupied by the C-terminal region of the subunit, rich in basic residues that interact with the DNA core.

Filamentous bacteriophages of the Ff family (especially M13) have been exploited as peptide display systems using two structural proteins of filamentous bacteriophage, the pIII (p3) protein and the pVIII protein, as display scaffolds for the peptides. Peptide epitopes have been displayed on filamentous phage for use in active immunization.

It has previously been demonstrated that filamentous bacteriophage, in particular M13, can disaggregate β-amyloid plaque (WO2006/083795; U.S. Pat. No. 7,867,487; and WO2008/011503) and α-synuclein aggregates (WO2010/060073). Filamentous bacteriophage displaying protein A as a binder for antibodies and immunocomplexes to be delivered to the brain is disclosed in WO2007/095616.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a filamentous bacteriophage for use in treating a neurodegenerative tauopathy or susceptibility to a neurodegenerative tauopathy, and a method for reducing the formation of fibrils of tau protein or disaggregating pre-formed fibrils of tau protein. The method involves administering to a patient in need thereof a filamentous bacteriophage which does not display (i) a mammalian cell internalization signal (ii) a β-amyloid antigen or an antibody to β-amyloid, or (iii) a tau protein antigen or an antibody to tau protein.

The present invention also provides a pharmaceutical composition containing a filamentous bacteriophage for use in treating a neurodegenerative tauopathy or susceptibility to a neurodegenerative tauopathy. The filamentous bacteriophage does not display (i) a mammalian cell internalization signal; (ii) a β-amyloid antigen or an antibody to β-amyloid; or (iii) a tau protein antigen or an antibody to tau protein.

BRIEF DESCRIPTION OF THE DRAWINGS

FIGS. 3A-3D show a quantitative microscope image analysis of thioflavin S (ThS) stained tangles in the cortex (FIGS. 3A and 3B) and hippocampal CA2 (FIGS. 3C and 3D) of the PBS treated hemisphere, −3.6 from Bregma. FIGS. 3B and 3D are enlarged views of the boxed area in FIGS. 3A and 3B, respectively. FIG. 3E is a graph showing the ThS tangles load in rTg4510+ mice as measured in % area occupied by ThS stained tangles.

FIGS. 4A and 4B show a quantitative image analysis of ThS stained plaques in 3×Tg mice. FIG. 4A is the PBS treated hemisphere and FIG. 4B is the M13 phage treated hemisphere. FIG. 4C is a graph showing the % area of ThS stained plaque load.

FIGS. 5A and 5B show a quantitative image analysis of the NeuN staining (labeled with mouse NeuN antibody) in the left (PBS treated) and right (phage treated) CA1 region of the hippocampus. FIG. 5C is a graph showing the % area labeled with mouse NeuN antibody.

DETAILED DESCRIPTION OF THE INVENTION

Definitions

Figure 1:
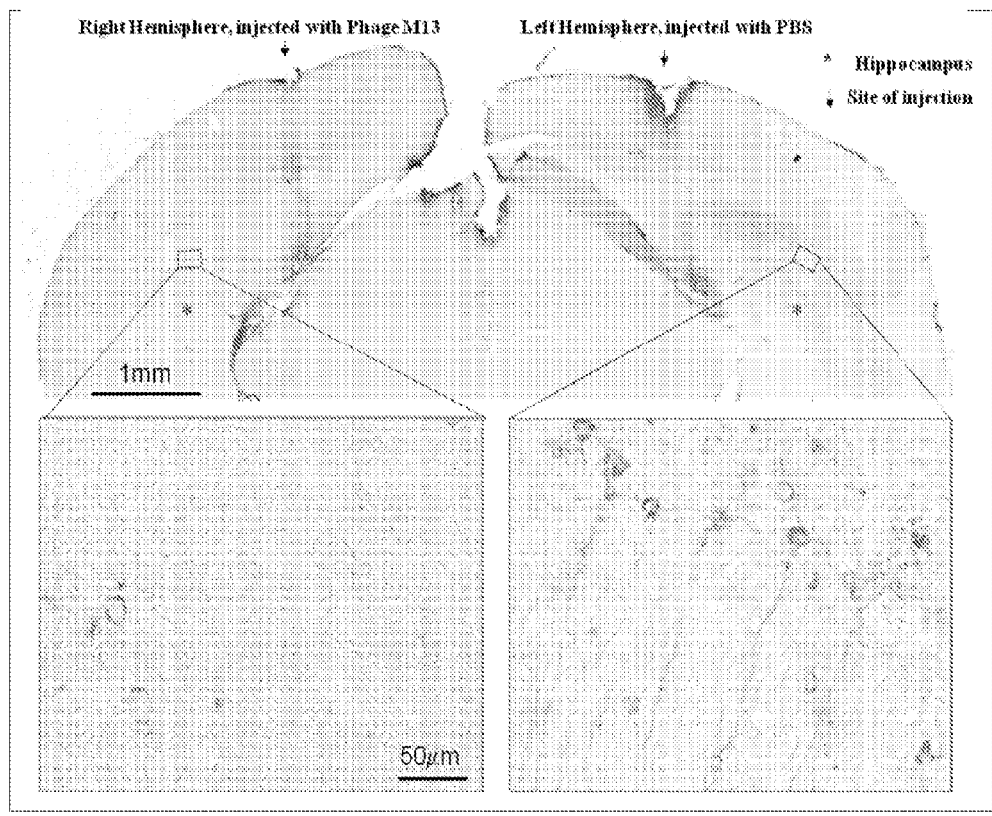
FIG. 1 depicts immunostaining of tau plaque following intrahippocampal WT filamentous bacteriophage M13 injection or PBS control in 3×Tg Mice. Brain section of 3×Tg mice at −3.6 from Bregma.

For purposes of this specification and the accompanying claims, the following definitions apply.

The terms "patient", "subject" and "recipient" are used interchangeably. They include humans and other mammals which are the object of therapeutic treatment.

The term "tau protein antigen" refers to any portion of the human microtubule-associated tau protein, e.g., any of the six naturally occurring isoforms of tau protein (see Lee et al., 2001), that is sufficient to induce an antibody that recognizes and specifically binds to at least one of the isoforms of tau protein. The term "an antibody to tau protein" refers to an antibody binding portion of an antibody that is induced by one of the isoforms of tau protein.

The term "neurodegenerative tauopathy" is intended to encompass neurodegenerative diseases or disorders characterized neuropathologically by intracellular deposits of abnormal filaments/fibrils/fibers of tau protein. Non-limiting examples of neurodegenerative tauopathies include Alzheimer's disease, Amyotrophic lateral sclerosis/parkinsonism-dementia complex, Argyrophilic grain dementia Corticobasal degeneration Creutzfeldt-Jakob disease Dementia, pugilistica, Diffuse neurofibrillary tangles with calcification, Down's syndrome, Frontotemporal dementia with parkinsonism linked to chromosome 17, Gerstmann-Straussler-Scheinker disease, Hallervorden-Spatz disease, Myotonic dystrophy, Niemann-Pick disease type C, Non-Guamanian motor neuron disease with neurofibrillary tangles, Pick's disease, Postencephalitic parkinsonism, Prion protein cerebral amyloid angiopathy, Progressive subcortical gliosis, Progressive supranuclear palsy, Subacute sclerosing panencephalitis, and Tangle only dementia.

The term "treating" with respect to a neurodegenerative tauopathy is intended to mean substantially inhibiting, slowing or reversing the progression of a neurodegenerative tauopathy, such as reducing or inhibiting the formation of fibrils/filaments/fibers of tau protein, or disaggregating pre-formed fibrils/filaments/fibers of tau protein; substantially ameliorating one or more clinical symptoms of a neurodegenerative tauopathy, or substantially preventing the appearance of clinical symptoms of a neurodegenerative tauopathy.

The term "antibody" as used herein includes polyclonal antibodies, monoclonal antibodies, antibody compositions with polyepitope specificities, bispecific antibodies, diabodies, or other purified preparations of antibodies and recombinant antibodies. The antibodies can be whole antibodies, e.g., of any isotype (IgG, IgA, IgE, IgM, etc.), or antibody fragments that bind the antigen of interest.

The term "mammalian cell internalization signal" refers to any cell adhesion sequence derived from mammalian sequences (e.g., not naturally occurring in wild-type filamentous bacteriophage) which facilitates internalization as a result of cell adhesion/attachment to the cell. Numerous mammalian cell adhesion sequences are known and include the Arg-Gly-Asp (RGD) cell adhesion sequence, the Tat peptide from HIV and peptides comprising the sequence of Arg-Glu-Asp (RED), Arg-Lys-Lys (RKK), Leu-Asp-Val (LDV; Humphries, 1992), Leu-Leu-Gly (LLG; Koivunen et al., 2001), Asp-Gly-Glu-Ala (DGEA; SEQ ID NO:1), Ile-Arg-Val-Val-Met (IRVVM; SEQ ID NO:2; Kosfeld et al., 1993), Pro-His-Ser-Arg-Asp (PHSRN; SEQ ID NO:3) and RFYV-VMWK (SEQ ID NO:4; Kosfeld et al., 1993). Many cell adhesion sequences (also known as cell attachment motifs) are known to exist in cell adhesive molecules such as laminin, fibronectin, vitronectin, fibrinogen, thrombospondin, etc.

The term "β-amyloid antigen" refers to any portion of a plaque forming "β-amyloid peptide", also known as "βAP", "βA", "Aβ" or "AβP", derived from human amyloid precursor protein, that induces the formation of a β-amyloid antibody. A "β-amyloid antibody" is one which recognizes and specifically binds naturally occurring human Aβ1-42 peptide and variants and mutants thereof.

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to a patient.

The phrases "physiologically acceptable carrier" and "pharmaceutically acceptable carrier," which may be interchangeably used, refer to a carrier or a diluent that does not cause significant irritation to an organism and does not abrogate the biological activity and properties of the administered compound.

The term "excipient" refers to an inert substance added to a pharmaceutical composition to further facilitate administration of an active ingredient. Non-limiting examples of excipients include calcium carbonate, calcium phosphate, various sugars and types of starch, cellulose derivatives, gelatin, vegetable oils and polyethylene glycols.

The term "wild-type filamentous bacteriophage" (or "wild-type" in conjunction with a specific filamentous bacteriophage, such as M13) as used herein means a naturally occurring filamentous bacteriophage that is isolated away from other components with which it is typically associated in nature. The term also includes commercially available filamentous phage that are characterized as "wild-type".

The term "inactivated wild-type filamentous bacteriophage" (or "inactivated wild-type" in conjunction with a specific filamentous bacteriophage, such as M13) as used herein means a wild-type filamentous bacteriophage that is not genetically altered by recombinant DNA means, but has been rendered incapable of replication, such as by UV-irradiation. Any mechanism which renders the phage incapable of replication, but does not disturb the filamentous structure of the bacteriophage (retains its ability to penetrate into the brain through the olfactory pathway) is contemplated by this invention.

The term "WT phage" (or "WT" in conjunction with a specific filamentous bacteriophage, such as M13) refers to both wild-type filamentous bacteriophage and inactivated wild-type filamentous bacteriophage.

Filamentous Bacteriophage for Use in Treatment and Methods of Treatment

In one embodiment, the invention provides a filamentous bacteriophage for use in treating a neurodegenerative tauopathy or susceptibility to a neurodegenerative tauopathy and a method for reducing the formation of fibrils of tau protein or disaggregating pre-formed fibrils of tau protein by administering to the patient a filamentous bacteriophage, wherein the bacteriophage does not display (i) a mammalian cell internalization signal, (ii) a β-amyloid antigen or an antibody to β-amyloid, or (iii) a tau protein antigen or an antibody to tau protein. In certain aspects of this embodiment, the filamentous bacteriophage does not display any non-filamentous bacteriophage polypeptide on its surface.

In some embodiments, the neurodegenerative tauopathy to be treated is selected from Amyotrophic lateral sclerosis, Argyrophilic grain dementia, Corticobasal degeneration, Creutzfeldt-Jakob disease, Dementia pugilistica, Diffuse neurofibrillary tangles with calcification, Down's syndrome, Frontotemporal dementia with parkinsonism linked to chromosome 17, Gerstmann-Straussler-Scheinker disease, Hallervorden-Spatz disease, Myotonic dystrophy, Niemann-Pick disease type C, Non-Guamanian motor neuron disease with neurofibrillary tangles, Pick's disease, Postencephalitic parkinsonism, Prion protein cerebral amyloid angiopathy, Progressive subcortical gliosis, Progressive supranuclear palsy, Subacute sclerosing panencephalitis, and Tangle only dementia. In a more specific aspect, the tauopathy is selected from Amyotrophic lateral sclerosis, Argyrophilic grain dementia, Corticobasal degeneration, Dementia pugilistica, Diffuse neurofibrillary tangles with calcification, Down's syndrome, Frontotemporal dementia with parkinsonism linked to chromosome 17, Hallervorden-Spatz disease, Myotonic dystrophy, Niemann-Pick disease type C, Non-Guamanian motor neuron disease with neurofibrillary tangles, Pick's disease, Postencephalitic parkinsonism, Progressive subcortical gliosis, Progressive supranuclear palsy, Subacute sclerosing panencephalitis, and Tangle only dementia.

In an alternate embodiment, the neurodegenerative tauopathy to be treated is other than Parkinson's disease; Alzheimer's disease, including early onset Alzheimer's disease, late onset Alzheimer's disease, and presymptomatic Alzheimer's disease; SAA amyloidosis; hereditary Icelandic syndrome; senility; multiple myeloma; and a prion disease that is known to affect humans, such as for example, kuru, Creutzfeldt-Jakob disease (CJD), Gerstmann-Straussler-Scheinker disease (GSS), and fatal familial insomnia (FFI) and animals, such as, for example, scrapie and bovine spongiform encephalitis (BSE).

In yet another embodiment, the neurodegenerative tauopathy to be treated is other than Parkinson's disease; Alzheimer's disease, Creutzfeldt-Jakob disease (CJD), Gerstmann-Straussler-Scheinker disease (GSS), and other prion diseases.

In one aspect of this embodiment, the bacteriophage is administered to the patient as part of a pharmaceutically acceptable composition additionally comprising a pharmaceutically acceptable carrier.

In another aspect of this embodiment, the bacteriophage is a WT phage. In still another aspect of this embodiment, the bacteriophage is a wild-type bacteriophage.

In one embodiment, the filamentous bacteriophage is administered intranasally. Without being bound by theory, applicants believe that intranasal administration allows these bacteriophage to cross the blood-brain barrier. The phage are then eliminated from the brain and body via intracellular degradation of phage, as well as by elimination from urine and feces without adverse effects on peripheral organs.

In another embodiment, the filamentous bacteriophage are administered directly to the brain of the subject. Administration "directly to the brain" includes injection or infusion into the brain itself, e.g., intracranial administration, as well as injection or infusion into the cerebrospinal fluid. In one aspect of this embodiment, administration is by intrathecal injection or infusion, intraventricular injection or infusion, intraparenchymal injection or infusion, or intracerebroventricular injection or infusion. In more specific aspects, administration is by intraparenchymal injection; intracerebroventricular injection; or intracerebroventricular infusion.

In yet another embodiment, the filamentous bacteriophage used in the present invention is WT M13. In a more specific embodiment, the filamentous bacteriophage used in the present invention is wild-type M13.

Methods delineated herein also include those wherein the patient is identified as in need of a particular stated treatment. Identifying a patient in need of such treatment can be in the judgment of a patient or a health care professional and can be subjective (e.g., opinion) or objective (e.g., measurable by a test or diagnostic method).

Pharmaceutical Compositions

In a related embodiment, the invention provides a pharmaceutical composition (e.g., pyrogen-free) for use in treating a neurodegenerative tauopathy or susceptibility to a neurodegenerative tauopathy comprising, and as the active ingredient, a filamentous bacteriophage which does not display (i) a mammalian cell internalization signal; (ii) a β-amyloid antigen or an antibody to β-amyloid, or (iii) a tau protein antigen or an antibody to tau protein. In certain aspects of this embodiment, the filamentous bacteriophage in the composition does not display any non-filamentous bacteriophage polypeptide on its surface. In a more specific aspect of this embodiment, the filamentous bacteriophage is a WT filamentous bacteriophage. In another more specific aspect of this embodiment, the filamentous bacteriophage is a wild-type filamentous bacteriophage. In still another specific aspect of this embodiment, the filamentous bacteriophage is a WT M13 bacteriophage. In a more specific aspect of this embodiment, the filamentous bacteriophage is a wild-type M13 bacteriophage.

Techniques for formulation and administration of drugs may be found in "Remington's Pharmaceutical Sciences," Mack Publishing Co., Easton, Pa., latest edition, which is incorporated herein by reference and are well known in the art.

Suitable routes of administration may, for example, include transnasal or parenteral delivery, including intramuscular, subcutaneous and intramedullary injections as well as administration directly to the brain, e.g., intracranial administration, as well as injection or infusion into the cerebrospinal fluid. In one aspect of this embodiment, administration is by intrathecal injection or infusion, intraventricular injection or infusion, intraparenchymal injection or infusion, or intracerebroventricular injection or infusion. In more specific aspects, administration is by intraparenchymal injection; intracerebroventricular injection; or intracerebroventricular infusion.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. A nasal spray, which does not require a pressurized pack or nebulizer as in an inhalation spray, can alternatively used for intranasal administration. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration or administration directly to the brain, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration or administration directly to the brain include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

Pharmaceutical compositions suitable for use in the context of the method of the present invention include compositions wherein the active ingredient(s) is contained in an amount effective to achieve the intended purpose. More specifically, an effective amount means an amount of active ingredient(s) effective to treat a neurodegenerative tauopathy.

Determination of a therapeutically effective amount is well within the capability of those skilled in the art, especially in light of the detailed disclosure provided herein.

Dosage amount and interval may be adjusted individually to provide brain levels of the filamentous bacteriophage which are sufficient to treat the particular neurodegenerative tauopathy (minimal effective concentration, MEC). The MEC will vary for each preparation and each particular neurodegenerative tauopathy, as well as the severity of the disease, but can be estimated from in vitro data. Dosages necessary to achieve the MEC will depend on individual characteristics.

In some embodiments, the MEC at the region of interest (e.g., the region containing pathologic tau aggregates) is between about $10^9$-$10^{13}$ filamentous phage particles/ml of tissue. Without being bound by theory, applicants believe that the dosage required to achieve this MEC is between about $10^{10}$-$10^{15}$ phage particles per administration. In a more specific embodiment, the dosage of phage in each administration is between about $10^{12}$-$10^{15}$ phage particles.

Dosage intervals can also be determined using the MEC value. Preparations should be administered using a regimen, which maintains brain levels above the MEC for 10-90% of the time, preferably between 30-90% of the time and most preferably between 50-90% of the time during the course of treatment. The number of administrations will vary depending upon the type and severity of the disease to be treated. In some embodiments, administration will be once a month at least until improvement of the condition is achieved. In other embodiments, administration will be once every two months, once every three months, once every four months, once every six months or once per year.

Depending on the severity and responsiveness of the neurodegenerative tauopathy to be treated in the patient, dosing can be of a single or a plurality of administrations, with the course of treatment lasting from several days to several weeks or until diminution of the neurodegenerative tauopathy state is achieved.

The amount of a composition to be administered will, of course, be dependent on the subject being treated, the severity of the affliction, the judgment of the prescribing physician, etc.

Compositions used in the method of the present invention may, if desired, be presented in a pack or dispenser device, such as an FDA approved kit, which may contain one or more unit dosage forms containing the active ingredient. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Having now generally described the invention, the same will be more readily understood through reference to the following examples which are provided by way of illustration and is not intended to be limiting of the present invention.

EXAMPLE 1

Filamentous Phage Activity on Tau Deposits in Transgenic Mouse Model

Materials and Methods

Animals: These experiments used adult mice 3×Tg-AD strain (Oddo et al., 2003) and rTg4510[+] mice (Santacruz et al., 2005). A colony of homozygous 3×Tg mice and wild type non-transgenic (NonTg) mice was established at the animal facilities of Tel-Aviv University. The triple transgenic AD mouse model (3×Tg-AD) has 2 familial AD-related gene mutations, mutant human amyloid precursor protein gene/presenilin protein 1 gene ($APP_{KM670/671NL}/PS1_{M146V}$), and a tau gene mutation ($Tau_{P301L}$). The model develops both plaque and tangle pathology with cognitive dysfunction in an age-dependent manner. rTg4510+ tau transgenic mice, males (n=5) and aged 13 months were kindly donated by Ed Stern (Bar-Ilan University, Israel). rTg4510 transgenic mice overexpress mutant (P301L) human tau protein linked to FTDP-17 specifically in the cortex, limbic system, and basal ganglia. The model is characterized by spatial memory deficits and the formation of a distinct 64 kDa abnormally hyperphosphorylated 4R0N isoform of tau and increase in neurofibrillary tangles (NFTs), with a rapidly progressing neuronal loss in the hippocampus by 5.5 months of age. All the experimental protocols were approved by the Tel-Aviv University Animal Care and Use Committees and all animal experimental procedures were performed according to Institutional Animal Care and Ethical Committee guidelines. Animals were kept 5 per cage at 12/12 light/dark conditions, with food and water available ad libitum.

Experimental Procedure: 15-month old AD 3×Tg mice (n=4) and 13-month rTg4510+ mice (n=5) were ipsilaterally injected with 2 μl of wild-type phage M13 ($1\times10^{14}$ virion/ml), and contralaterally injected with 0.01M PBS as an inner control. Briefly, mice were anesthetized with Ketamine (100 mg/kg)/Xylazine (10 mg/kg, i.p), placed on stereotaxis (Narishige, Scientific instrument Lab, SRS-5) upon warming carpet. The mice were fixed. Sedation was monitored using a gentle toe pinch withdraw reflex. Thermoregulation was provided through a thermostat regulated heating pad, and monitored through an abdominal thermometer. Head was shaved of fur, cleaned with iodine and skin incision (1 cm long for mice) was done by sterile scalpel and all soft tissue was removed from the surface of the skull. The Hamilton syringe with 32 g needle was placed in relation to bregma. A hole was drilled through the skull with a battery-operated driller designed for rodent surgery (Fine Science Tools, Inc.). Care was taken so that the drill bit did not penetrate through meningeal membranes or blood vessels.

Stereotaxic coordinates established as per Franklin and Paxinos, 1997 (The Mouse Brain in Stereotaxic Coordinates, Academic Press) were: Bregma −2.5 mm; Interneural 2 mm; Dorsoventral 2 mm. A bolus of pre-warmed Lactated Ringers of the 0.9% saline was given at the end of surgery (3 ml s.c.) to prevent dehydration. Buprenorphine (0.1-0.5 mg/kg s.c.) was administered once. Antibiotic injection (tetracyline 5 mg/kg i.p.) was administered to prevent and circumvent concomitant and post-operative infections.

Following surgery, animals were housed within their cages with food and water available ad libitum. One week later the mice were killed by an exposure to $CO_2$ and their brains were collected, fixed by immersion in 4% paraformaldehyde, followed by 30% sucrose cryoprotection, frozen by dry nitrogen oxide and cut by cryostat to 25 μm in coronal axis in rostrocaudal direction, and stored in a solution consisting of 30% glycerin, 30% ethylene glycol, in 0.1M phosphate buffer at −20.0 until processed for histological immunohistochemistry.

ThS Staining: The effect of Phage M13 treatment on tau pathology was evaluated using the improved Thioflavin-S (ThS) method (Sun et al., 2002). The sections were immersed into ThS (0.01% in 50% ethanol) for 8 min incubation in the dark, then dipped in 80% ethanol for 10 sec 2 times, rinse with $dH_2O$ and mounted.

Immunohistochemistry: Brain tissues were processed as free-floating sections and stained with anti-NeuN and anti-tau AT8 antibodies. All antibodies were diluted in TBS pH 7 containing 0.1% Triton X-100, 0.05% Tween 20 ($TBS^+$). Primary antibodies were also supplemented with 3% donkey serum ($TBS^{++}$). The primary antibodies used were: mouse α-neuron-specific nuclear protein; (NeuN) (1:200; Zymed™, Invitrogen, Carlsbad, Calif., USA); Anti-PHF-tau antibody clone AT8 has been shown to detect PHF-tau doubly phosphorylated at Ser202 and Thr205, serines 199 and 202, and serines 205 and 208 (1:250, Innogenetics, Ghent., Belgium). Broad-range polymer-HRP (ready to use, Invitrogen, Carlsbad, Calif.) was used as secondary antibodies for light microscopy and was developed by 3,3-diaminobenzedine tetrahydrochloride (DAB kit, Vector Laboratories inc. Burlingame, Calif.).

Free floating sections from the site of injection and from each 100 μm increment, proximally and distally to the site of injection were taken from each animal. Sections were washed 3×10 min in phosphate buffer and 3×10 min in Tris buffered saline (TBS) to remove cryoprotectant, followed by 10 min 3% $H_2O_2$ in absolute methanol to quench endogenous peroxidase activity. Antigen retrieval with 90% formic acid (5 min, r.t.) was applied only for AT8 antibody. Sections were blocked 10 min with UV Block (ready to use, ThermoFisher, MI, USA) and additionally for 30 min with 10% Fetal calf serum in PBS at r.t, and followed by o.n. incubation with primary antibody on an orbital shaker at 45 RPM. Picture plus Polymer-HRP was applied for 20 min and then developed with DAB.

Image Analysis: Microscopic evaluation was performed using a Leica DMLB microscope at a magnification of ×400. Images of two well-defined coronal sections at the levels of −2.8 and −3.5 from bregma, respectively, were obtained via a CCD color video camera (ProgRes C14, Jenoptic, Jena, Germany) and analyzed with ImageJ tool software (NIH). The total TAU load was measured and expressed as a percentage of the $ThS^+$ stained area of the total area of the section. Results are presented as the mean tangle load of two sections. The effect of Phage M13 injection on phosphorylated TAU pathology was evaluated by counting the number of $AT8^+$ cells per hippocampal area in 3×Tg mice. The specified objects per area of $NeuN^+$ neurons in the hippocampal CA1 region were estimated for 3×Tg mice.

Statistical Analyses: Data are presented in the text as mean±SEM. Statistical differences between groups were determined by two-tailed t-test, with planned comparisons between groups (Tg control vs. Tg treated). For analysis of three and more variables, one way Anova was used, followed by post hoc comparison testing. For all analyses, P<0.05 was considered significant. Statistical analyses were performed using SPSS Software (SPSS Inc., Chicago, Ill.).

Results

Phage M13 Effect on Phosphorylated TAU in 3×Tg Mice

Figure 2:
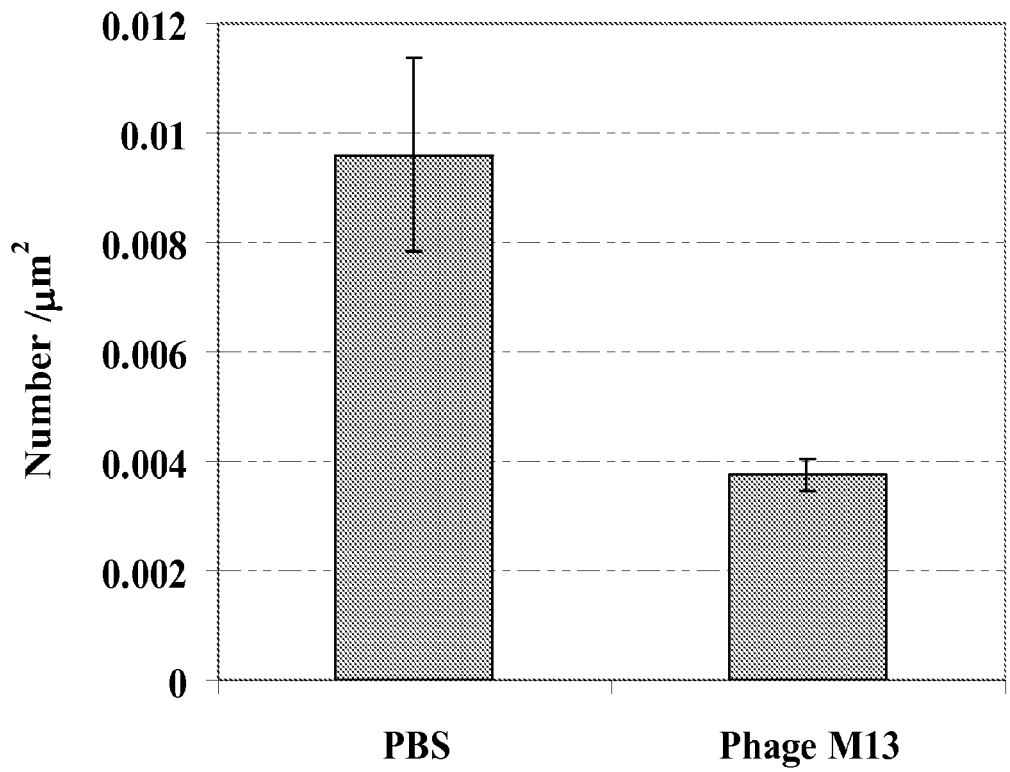
FIG. 2 is a graph of the results from FIG. 1 showing the calculated number of tau tangles per hippocampal area.

In order to evaluate the effect of treatment on the brain tau tangles, the brains were immunostained with anti-tau AT8 antibody (FIG. 1). The number of tangles per hippocampal area were calculated and shown to be significantly reduced (AT8 positive cells) in the hippocampus of 3×Tg mice that received the injection of M13 as compared to the PBS-treated hemisphere (FIG. 2).

Phage M13 Effect on Tangles Load in the Brain in rTg4510+ Mice

The measurement of the area occupied by ThS stained tangles (FIGS. 3A-3D) per whole hemisphere area demonstrated the powerful trend (P=0.07) towards reduction of tangles load in the hippocampal area and the significant reduction (p=0.025) in the cortex of phage M13-treated hemisphere vs PBS-treated (FIG. 3E).

Phage M13 Beneficial Effect on ThS Plaque Load in 3×Tg Mice.

The quantitative image analysis of ThS stained plaques in 3×Tg mice demonstrated the 26% reduction in amyloid plaque load in phage M13-treated hemisphere vs PBS-treated hemisphere (FIGS. 4A-4C). The reduction in ThS stained plaque load was observed in subicullum related to phage M13-treated hemisphere. In addition, amyloid plaques in the treated hemisphere have smaller size.

Phage M13 Effect on NeuN Labeling in 3×Tg Mice.

Quantitative image analysis of the NeuN load demonstrated almost similar NeuN positive neurons distribution between phage-treated (FIG. 5B) and PBS-treated (FIG. 5A) hemispheres. The % area of NeuN load in both hemispheres is shown in FIG. 5C. This result provides evidence that phage intrahippocampal injection was not toxic for neurons, similar to PBS.

From the results of the above experiments, it can be concluded that:
1. Phage M13 injection significantly reduced the number of AT8 positive cells in 3×Tg mice.
2. Phage M13 injection has significant beneficial effect on tangles load in rTg4510+ mice brains.
3. Phage M13 injection caused reduction in amyloid plaque load in 3×Tg mice.
4. Phage M13 injection has no effect on NeuN labeling between the hemispheres in 3×Tg transgenic and normal C57/B mice. This finding suggests that phage M13 is not toxic as the number of remaining neurons is similar to PBS.
5. The similarity in NeuN staining between phage and PBS treated hemispheres suggests that the effect arises from the direct impact of the phage on tau pathology.

Accordingly, phage M13 has direct beneficial effect on tau, and the reduction in tangles load in TAU Tg mice provide evidence for direct phage action on tau in vivo.

EXAMPLE 2

Disaggregation of Tau Fibrils Treated with Filamentous Phage

Cellulose acetate membrane filter selectively retains fibril conformers of tau. One of the original protocols for filter retardation assays for amyloid-like protein aggregates is Wanker et al. (1999).

Materials and Methods

Preparation of Tau Fibers: Tau fibers were assembled as described in Margittai and Langen (2006).

Tau fibers were diluted into PBS (final concentration 2.5 µM) containing different concentrations ($1\times10^{12}$ and $1\times10^{13}$ phage/ml) of wild type M13 bacteriophage and incubated for three days at 37° C. At the end of the reactions, serial dilutions of the tau fibrils were subjected to filtration through a cellulose acetate membrane filter that selectively retains cross-β sheet amyloid, followed by immunoblotting (primary antibody was diluted as described by the supplier in 5% non-fat milk for 1 hr at room temperature; secondary antibody: anti-mouse IgG peroxidase conjugate from Sigma Fine Chemicals, St. Louis, diluted 1:30000 in 5% non-fat milk for 1 hr at room temperature) to show the amount of tau fibers retained on the filter in order to quantitate disaggregation of tau fibers. The antibody used for immunoblotting was anti-tau antibody EP2456Y (Millipore) for detecting f-tau.

Results

Figure 6:
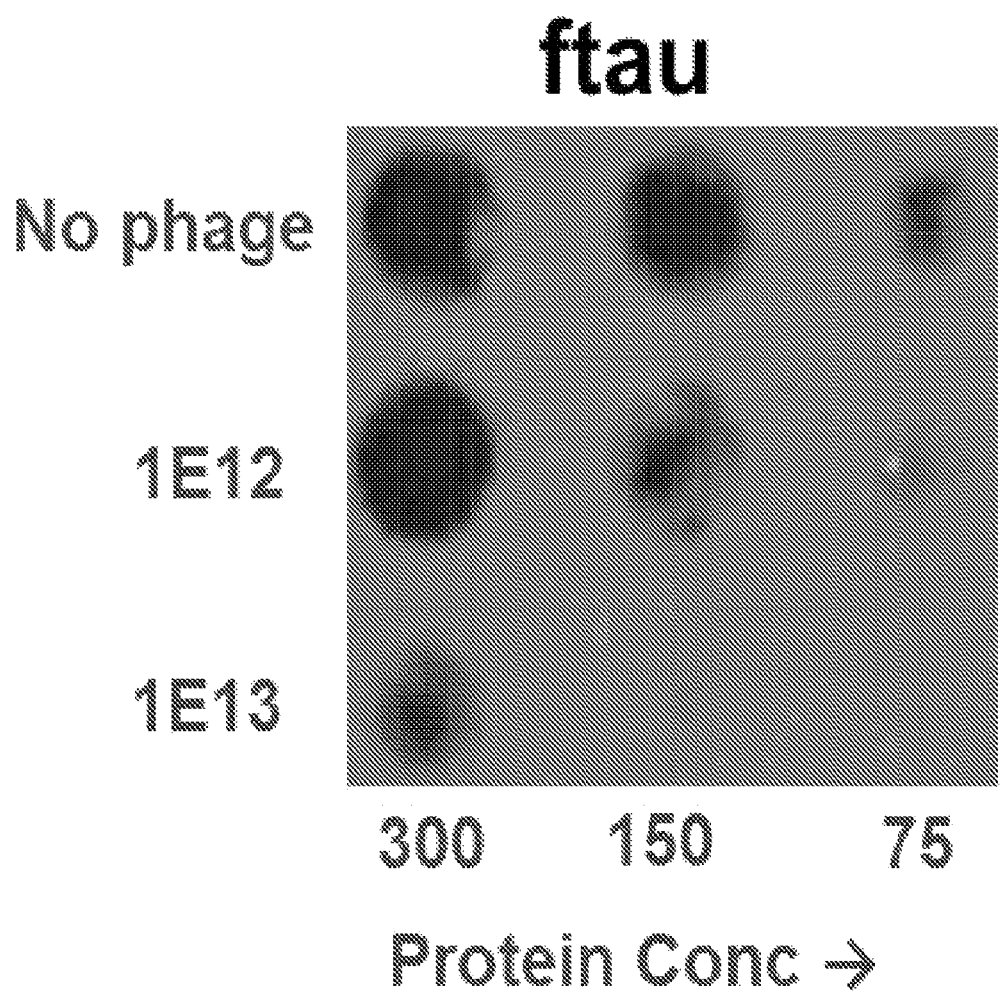
FIG. 6 shows disaggregation of tau fibrils by M13 phage as determined by a cellulose acetate membrane filter retardation assay.

As shown in FIG. 6, M13 converts fibrils of tau in a concentration-dependent manner to disaggregated/dissociated species that fail to be retained by the cellulose acetate membrane filter.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Gendron et al., Molecular Neurodegeneration, *Molecular Nerodegneration*, 4:(13)1-19 (2009)

Hanger et al., Tau phosphorylation: the therapeutic challenge for neurodegenerative disease, *Trends in Molecular Medicine*, pages 1-8 (2009)

Humphries, Peptide recognition motifs involved in the binding of integrins to their ligands, *Kidney International*, 41:645-649 (1992)

Koivunen et al., "Inhibition of $\beta_2$ integrin-mediated leukocyte cell adhesion by leucine-leucine-glycine motif-containing peptides, *The Journal of Cell Biology*, 153(5):905-915 (2001)

Kosfeld et al., "Identification of a new cell adhesion motif in two homologous peptides from the COOH-terminal cell binding domain of human thrombospondin" *The Journal of Biological Chemistry*, 268(12):8808-8814 (1993)

Lee et al., Neurodegenerative Tauopathies, *Annu. Rev. Neurosci.*, 24:1121-1159 (2001)

Lee, E N, Cho, H. J, Lee, C. H., Lee, D, Chung, K. C, & Palk, S. R. Phthalocyanine tetrasulfonates affect the amyloid formation and cytotoxicity of alpha-synuclein. *Biochemistry*, 43:3704-3715 (2004)

Oddo et al., *Neuron*, 39(3):409-421 (2003)

Pritchard et al., The toxicity of tau in Alzheimer disease: turnover, targets and potential therapeutics, *J. Cell. Mol. Med.*, 15(8):1621-1635 (2011)

Wanker et al., *Methods Enzymol.* 309:375-386 (1999)

Margittai and Langen, *Meth. Enzymol.* 413:122-139 (2006)

Santacruz et al., *Science*, 309(5733):476-481 (2005)

Sun et al., *J. Histochem. Cytochem.*, 50(4):463-472 (2002)

---

What is claimed is:

1. A method for reducing the formation of fibrils of tau protein or for disaggregating pre-formed fibrils of tau protein in a patient, comprising administering to the patient in need thereof a filamentous bacteriophage in an amount effective to achieve such reduction or disaggregation, wherein:

the patient is not suffering from Alzheimer's Disease, including early onset Alzheimer's disease, late onset Alzheimer's disease, presymptomatic Alzheimer's disease; SAA amyloidosis; hereditary Icelandic syndrome; senility; multiple myeloma; kuru; Creutzfeldt-Jakob disease (CJD); Gerstmann-Straussler-Scheinker disease (GSS); other prion diseases, fatal familial insomnia (FFI) or Parkinson's Disease; and the filamentous bacteriophage is a filamentous bacteriophage selected from the group consisting of M13, f1 and fd bacteriophage, and mixtures thereof and does not display (i) a mammalian cell internalization signal, (ii) a β-amyloid antigen or an antibody to β-amyloid, or (iii) a tau protein antigen or an antibody to tau protein.

2. The method of claim 1, wherein the filamentous bacteriophage does not display any non-filamentous bacteriophage polypeptide on its surface.

3. The method of claim 1, wherein the filamentous bacteriophage is a wild type filamentous bacteriophage.

4. The method of claim 1, wherein the filamentous bacteriophage is a wild-type M13 bacteriophage.

5. The method of claim 1, wherein the patient is suffering from a neurodegenerative tauopathy selected from the group consisting of Argyrophilic grain dementia, Corticobasal degeneration, Dementia pugilistica, diffuse neurofibrillary tangles with calcification, Down's syndrome, Frontotemporal dementia with parkinsonism linked to chromosome 17, Hallervorden-Spatz disease, Myotonic dystrophy, Niemann-Pick disease type C, Non- Guamanian motor neuron disease with neurofibrillary tangles, Pick's disease, Postencephalitic parkinsonism, Progressive subcortical gliosis, Progressive supranuclear palsy, Subacute sclerosing panencephalitis, and Tangle only dementia.

6. The method of claim 1, wherein the administration to the patient is directly to the brain.

7. The method of claim 1, wherein administration to the patient is selected from intraparenchymal injection or infusion; intracerebroventricular injection; injection into the intrathecal space; and intracerebroventricular infusion.

8. A method for treating a neurodegenerative tauopathy other than Alzheimer's Disease, Creutzfeldt-Jakob disease (CJD); Gerstmann-Straussler-Scheinker disease (GSS); other prion diseases, or Parkinson's Disease in a patient, comprising the step of administering to the patient in need thereof a pharmaceutically acceptable composition comprising:

(a) an effective amount of a filamentous bacteriophage, wherein the filamentous bacteriophage is selected from the group consisting of M13, f1 and fd bacteriophage, and mixtures thereof and does not display: (i) a mammalian cell internalization signal, (ii) a β-amyloid antigen or an antibody to β-amyloid, or (iii) a tau protein antigen or an antibody to tau protein; and (b) a pharmaceutically acceptable carrier.

9. The method of claim 8, wherein the neurodegenerative tauopathy to be treated is selected from the group consisting of Argyrophilic grain dementia, Corticobasal degeneration, Dementia pugilistica, diffuse neurofibrillary tangles with calcification, Down's syndrome, Frontotemporal dementia with parkinsonism linked to chromosome 17, Hallervorden-Spatz disease, Myotonic dystrophy, Niemann-Pick disease type C, Non-Guamanian motor neuron disease with neurofibrillary tangles, Pick's disease, Postencephalitic parkinsonism, Progressive subcortical gliosis, Progressive supranuclear palsy, Subacute sclerosing panencephalitis, and Tangle only dementia.

10. The method of claim 8, wherein the filamentous bacteriophage does not display any non-filamentous bacteriophage polypeptide on its surface.

11. The method of claim 8, wherein the filamentous bacteriophage is a wild type filamentous bacteriophage.

12. The method of claim 8, wherein the filamentous bacteriophage is an inactivated filamentous bacteriophage.

13. The method of claim 8, wherein the administration to the patient is directly to the brain.

14. The method of claim 8, wherein administration to the patient is selected from intraparenchymal injection or infusion; intracerebroventricular injection; injection into the intrathecal space; and intracerebroventricular infusion.

* * * * *